United States Patent [19]

Fougman

[11] 4,143,445

[45] Mar. 13, 1979

[54] FIXATION DEVICE

[75] Inventor: Arthur Fougman, Sollentuna, Sweden

[73] Assignee: Siemens Aktiengesellschaft, Berlin & Munich, Fed. Rep. of Germany

[21] Appl. No.: 887,475

[22] Filed: Mar. 17, 1978

[30] Foreign Application Priority Data

Apr. 1, 1977 [DE] Fed. Rep. of Germany ....... 2714695

[51] Int. Cl.² ............................................. A44B 21/00
[52] U.S. Cl. .................................... 24/68 R; 128/134; 254/51
[58] Field of Search .............. 24/68 R, 68 SB, 68 AS, 24/68 CD, 68 B, 68 D, 269, 270; 254/51, 79, 161; 128/134; 248/499; 52/DIG. 11

[56] References Cited

U.S. PATENT DOCUMENTS

| 2,521,191 | 9/1950 | Stanland | 254/161 |
|---|---|---|---|
| 2,815,189 | 12/1957 | Woods | 254/51 |
| 3,430,303 | 3/1969 | Perrin et al. | 24/269 |

FOREIGN PATENT DOCUMENTS 2610830  9/1977  Fed. Rep. of Germany .......... 128/134

Primary Examiner—Kenneth J. Dorner
Attorney, Agent, or Firm—Hill, Gross, Simpson, Van Santen, Steadman, Chiara & Simpson

[57] ABSTRACT

In the illustrated embodiment, a patient fixation strap is releasably secured to a roller which is freely rotatable on the shaft of a control handle. A spring is coiled on a stationary stop and has one end engageable with the roller so that a slight rotation of the roller due to strap tension wraps the spring tightly on the stop to hold the strap. If the handle is turned to further increase strap tension, an entrainment member fixed to the shaft engages the roller and moves the roller against the spring end in the spring unwinding direction to release the stop. If the handle is turned to release strap tension, the same entrainment member acts on the opposite end of the spring in the spring unwinding direction. Thus tension and release of the strap can be accomplished with one hand.

3 Claims, 3 Drawing Figures

FIXATION DEVICE

BACKGROUND OF THE INVENTION

The invention relates to a fixation device for a patient, including a fixation or strap, one end of which is fastened to a rotatable roll which rotates with the aid of a handle, which is mounted on a shaft, and which is fastened by means of a manually releasable blocking arrangement for blocking the roll in the direction of strap release, and wherein the handle is fastened to the shaft and the shaft is positioned rotatably in a holding means.

A fixation apparatus of this type is known from prior art and used for fixedly positioning a patient in case of X-ray examinations. The fixation strap thereby is tensioned and/or loosened with the aid of a handle fixedly connected to the roll. In order to arrest or release the roll and/or the fixation strap the operator must hold the handle with one hand and actuate the blocking arrangement with the other hand.

SUMMARY OF THE INVENTION

The invention is based on the problem of creating a fixation apparatus of the initially mentioned type where upon releasing the handle the fixation strap is arrested automatically, so that the fixation strap can be tensioned and released with one hand.

According to the invention this problem is solved in that the roll of the fixation apparatus is positioned freely rotatably on the shaft, that the holding means has in the area of one bearing for the shaft a stationary hollow-cylindrical extension, that a spring is firmly coiled about the extension, the free ends of said spring protruding, that at least one stop of the roll so coacts with one spring end that, as the strap is pulled off the roll it urges against this spring end and keeps the spring taut, and that between both spring ends an entrainment means fastened to the shaft is arranged which upon rotation of the shaft in either of the two opposite directions so acts on the spring ends that the spring is released from the extension.

In the fixation apparatus according to the invention the roll is released as the handle is rotated in either direction. Upon releasing the handle, the roll, and with it, the fixation strap will be arrested.

Additional advantages and details of the invention can be read from the dependent claims.

Below the invention is explained in greater detail by way of the embodiment exemplified in the accompanying sheet of drawings; other objects, features and advantages will be apparent from this detailed disclosure and from the appended claims.

DETAILED DESCRIPTION

Figure 1:
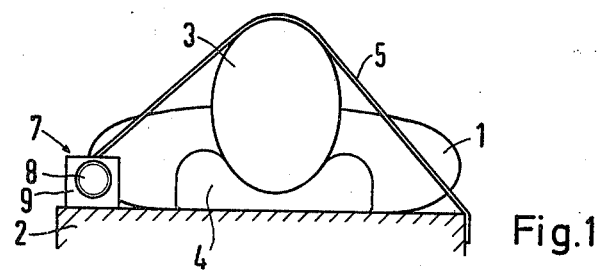
FIG. 1 shows a schematic representation of a patient positioned by means of the fixation apparatus according to the invention.

FIG. 1 shows a patient 1 placed on a cot 2 and whose head 3 rests on a pillow 4. The head 3 of the patient 1 is fixed with the aid of a fixation strap 5 for a medical examination, for example an X-ray examination; one end of said strap is coiled on a roll 6 (FIG. 2) of a fixation apparatus 7, while the other end is fastened to the lower longitudinal side of the cot 2. The fixation strap 5 is tensioned by counterclockwise rotation of a handle 8 and loosened by clockwise rotation of the handle. As the handle 8 is released by the operator, the strap 5 is arrested.

Figure 2:
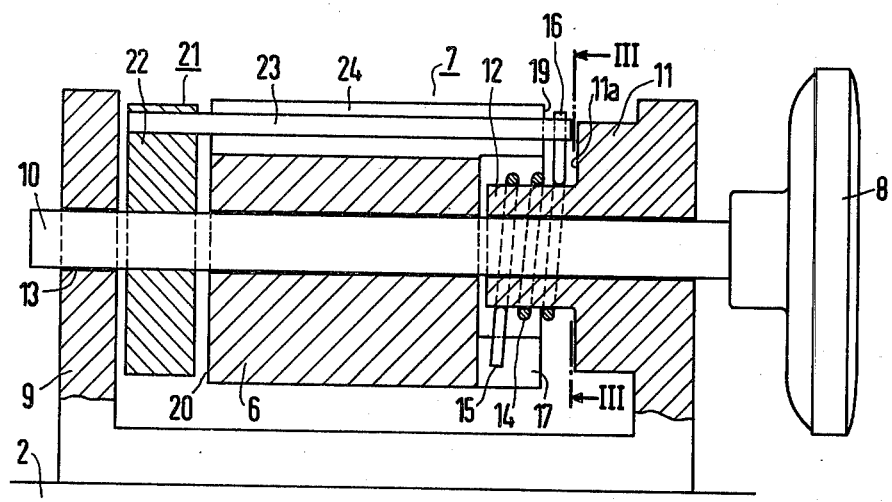
FIG. 2 shows a fixation apparatus according to the invention in longitudinal section.

FIG. 2 shows that the roll 6 is positioned freely rotatably on a shaft 10 which in turn is positioned rotatably in a holding means 9. The shaft 10 is supported on the one hand in a hollow-cylindrical bearing bushing 11 with a likewise hollow-cylindrical extension or stop 12 which extends into a suitable cavity of the roll 6, and on the other hand in a cylindrical bore 13 present in the holding means 9. The handle 8 is fastened at one end of the shaft 10. A spring 14 whose free ends 15, 16 protrude is firmly coiled about the extension 12. The first spring end 15 is placed between two spaced stops 17, 18 (FIG. 3) of the roll 6, and the second spring end 16 is placed with respect to the axial direction between the one frontal side 19 of the roll 6 and the frontal side 11a (FIG. 2) of the bushing 11. An entrainment means 21 includes a disc 22 placed on the shaft 10 between the other frontal side 20 of the roll 6 and the holding means 9. The disc 22 is fastened to the shaft 10 and a pin 23 is fastened to the disc 22. The pin 23 extends through a groove 24 formed in the roll 6, and its free end is located between the spring end 16 and the sidewall 25 (FIG. 3) of the groove 24.

Figure 3:
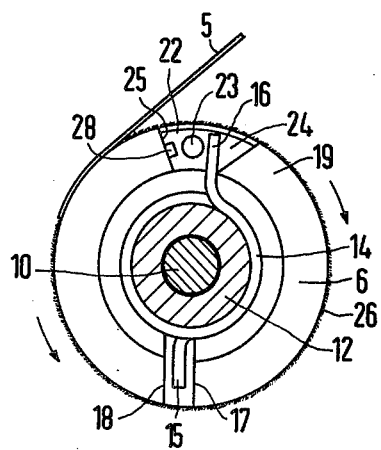
FIG. 3 is a section through the fixation apparatus according to FIG. 2, along line III—III.

FIG. 3 shows that the surface of the roll 6 is coated with a burdock strap 26 on which the fixation strap 5 is fastened. As the fixation strap 5 is pulled in the traction direction, the roll 6 is rotated slightly clockwise. The stop 17 of the roll 6 presses against the spring end 15. In the view according to FIG. 3 the spring 14 is firmly coiled clockwise on the stop or extension 12, so that it is tensioned, that is pulled or wrapped firmly on the stop 12, thus braking the roll 6.

As the shaft 10 and the entrainment means 21 are rotated clockwise with the aid of the handle 8 (FIG. 3), for loosening the strap 5, the pin 23 presses against the spring end 16, so that the spring is loosened from the extension or stop 12. In this direction the roll 6 thus is freely rotatable. As the handle 8 is released, the spring end 15 returns to its initial condition with stop 17 acting thereon, and the roll 6 is arrested again in the manner mentioned. Under the counterclockwise rotation of the handle 8 (FIG. 3), that is as the strap 5 is being tensioned, the pin 23 presses against an adjustment screw 28 in the lateral wall 25 of the groove, thereby pressing the stop 18 against the spring end 15 and loosening the spring 14 from the extension or stop 12. Thus, the roll 6 is freely rotatable in this direction likewise, except as it is held by the fixation strap 5. As the handle 8 is released, the spring end 15 returns to its original condition and the roll 6 is again arrested in the manner described. The distance between the roll and the spring end 16 is adjustable by means of the adjustment screw 28.

Within the scope of the invention each end of the fixation strap 5 also may be fastened on one fixation apparatus each of the described kind which is mounted on one longitudinal side each of the cot 2. By rotating the handles of both fixation devices in the same direction, it is possible thereby to adjust the position of the head 3 of the patient 1.

The groove between the stops 17 and 18 may be dispensed with by applying the spring end 15 between the lateral wall 25 (FIG. 3) and the pin 23 of the entrainment means 21.

It will be apparent that many modifications and variations may be effected without departing from the scope of the novel concepts and teachings of the present invention.

I claim as my invention:

1. A fixation device for a patient, including a fixation strap, a rotatable roll for fastening one end of the strap, a shaft mounting the rotatable roll for rotation, holding means for rotatably mounting the shaft, a handle fastened to the shaft, and a manually releasable blocking arrangement for blocking the roll in the direction of release of strap tension, characterized by the fact that the roll (6) is freely rotatably on the shaft (10), that the holding means (9) has a stationary generally cylindrical stop means (12), that the blocking arrangement comprises a spring (14) firmly coiled about the cylindrical stop means (12), the free ends (15, 16) of said spring protruding, at least one control stop (17) of the roll (6) coacting with one spring end (15) so that, as the strap (5) is pulled off the roll (6) the control stop (17) acts against said spring end (15) and keeps the spring (14) taut, and an entrainment means (21) fastened to the shaft (10) and arranged between both spring ends (15, 16), and operable upon rotation of the shaft (10) in either of its directions of rotation to act on the spring ends (15, 16) so that the spring (14) is released from the cylindrical stop means (12).

2. A fixation device as defined in claim 1, characterized by the fact that the spring end (15) coacting with the roll (6) is placed between two control stops (17, 18) of the roll (6) which are in spaced relation, and that the entrainment means (21) is located between the spring end (16) and a third control stop (25, 28) of the roll (6), so that upon rotation of the shaft (10) in one direction, the entrainment means (21) presses against the spring end (16) associated with it and releases the spring (14) from the cylindrical stop means (12), while upon rotation in the opposite direction it presses against the third control stop (25, 28) thereby urging one of the control stops (17, 18), between which the other spring end (15) is located, against said spring end (15), and releases the spring (14) from the cylindrical stop means (12).

3. A fixation apparatus as defined in claim 2, with at least one of the control stops (17;18; 25, 28) being adjustable in relation to the associated spring end (15, 16).

* * * * *